United States Patent [19]
Wilkes et al.

[11] Patent Number: 5,743,888
[45] Date of Patent: Apr. 28, 1998

[54] SAFETY NEEDLE

[75] Inventors: Robert D. Wilkes, Galveston, Tex.; Paul S. Turin, Berkeley, Calif.; Robert G. Ullrich, Alameda, Calif.; Brian S. Murray, Oceanside, Calif.

[73] Assignee: Kaleva Design, San Leandro, Calif.

[21] Appl. No.: 687,842

[22] Filed: Jul. 26, 1996

Related U.S. Application Data

[60] Provisional application No. 60/001,741 Aug. 1, 1995.
[51] Int. Cl.⁶ .................................................. A61M 5/32
[52] U.S. Cl. .................................................. 604/198; 604/192
[58] Field of Search .................................................. 604/198, 192

[56] References Cited

U.S. PATENT DOCUMENTS

| | | | |
|---|---|---|---|
| 4,139,009 | 2/1979 | Alvarez | 604/198 |
| 5,554,122 | 9/1996 | Emanuel | 604/198 |

*Primary Examiner*—Michael Buiz
*Assistant Examiner*—Julian W. Woo
*Attorney, Agent, or Firm*—John J. Murphey, Esq.; Murphey Law Offices

[57] ABSTRACT

An improved safety needle, including a needle base, for fixing therein a rigid needle containing a hollow hub at one end, a hollow needle connected thereto and a sharp needle tip at the other end, the base defined by a proximal end and a distal end spaced-apart therefrom, the distal end of the needle base having formed therethrough a first bore concentric to the needle and covering the sharp needle tip, and a cap covering the first bore and rotatably positioned thereover, having formed therethrough a second bore, wherein the cap is rotatable between a first, safe position placing the first and second bores out of alignment and preventing passage of the needle and the sharp needle tip therethrough, and a second, armed position placing the first and second bores in alignment to allow passage of the needle therethrough to expose the sharp needle tip.

78 Claims, 9 Drawing Sheets

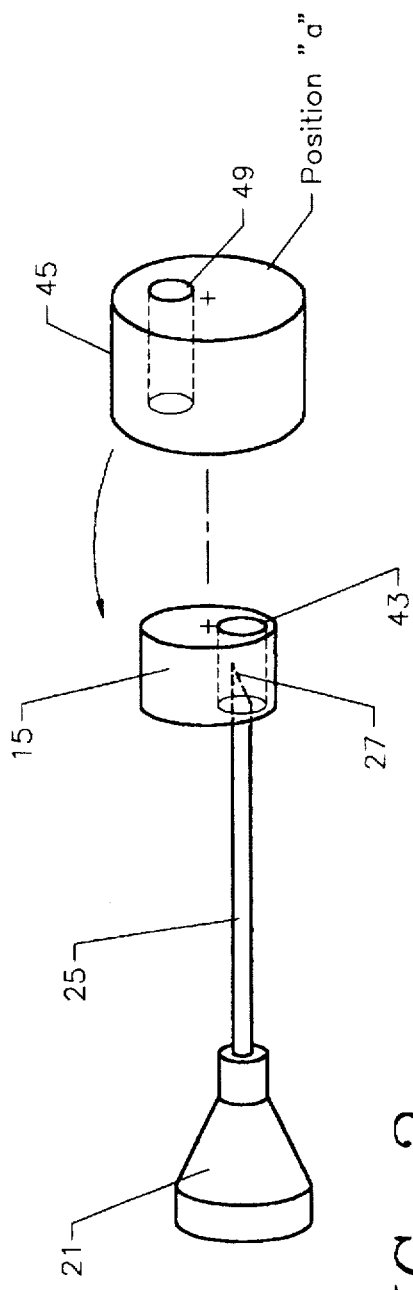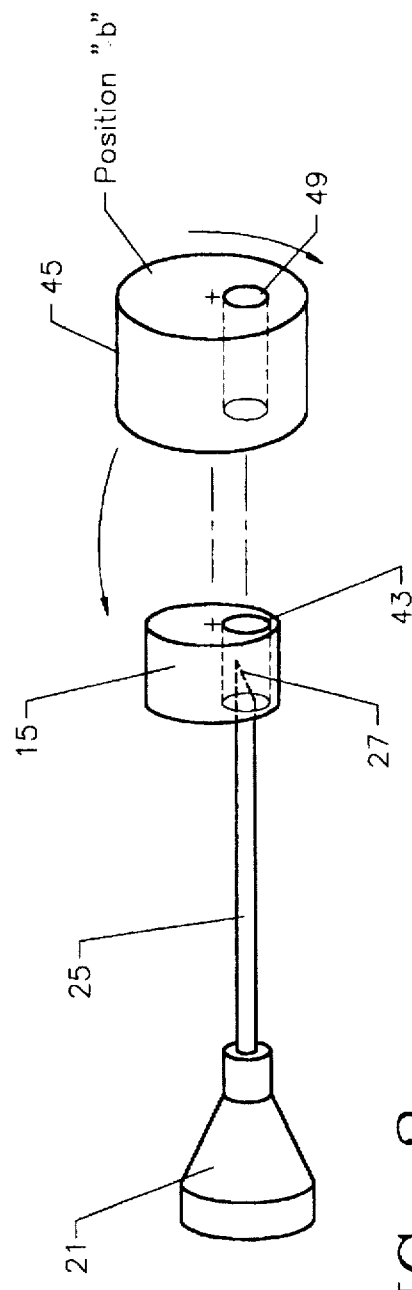

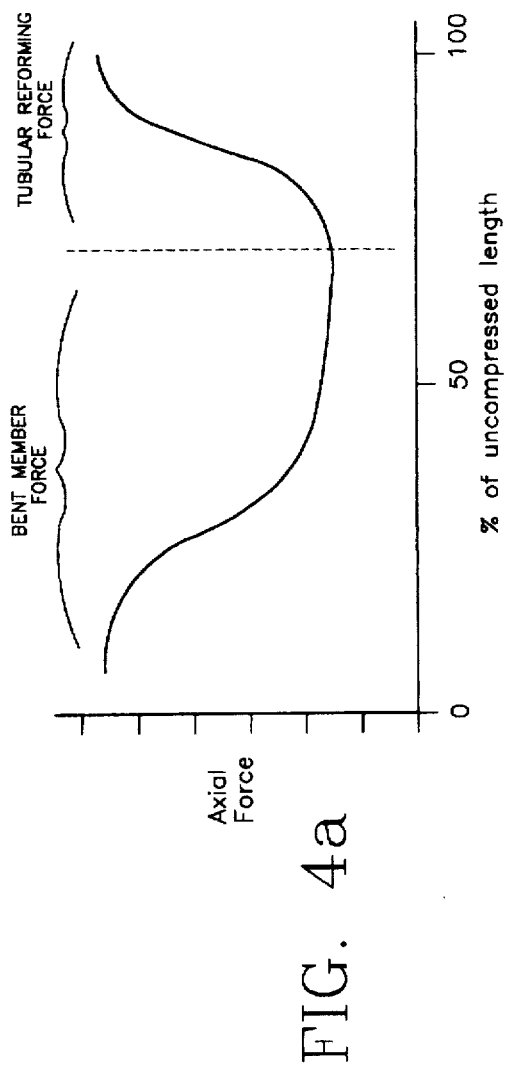
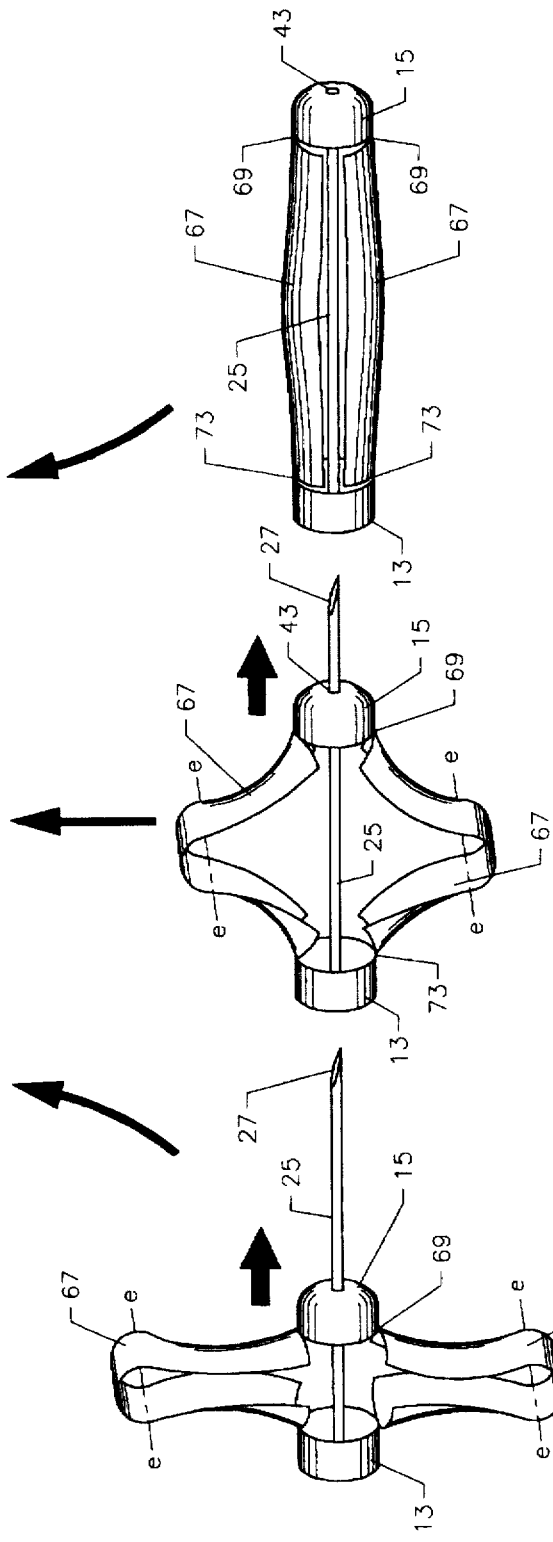
FIG. 4a  FIG. 4b  FIG. 4c  FIG. 4d

SAFETY NEEDLE

RELATION TO OTHER APPLICATIONS

This application is a utility patent application of our previous provisional patent application, Ser. No. 60/001,741, filed Aug. 1, 1995, titled SAFETY NEEDLE.

BACKGROUND OF THE INVENTION

1. Field of the Invention

This invention pertains to the field of medical appliances. More particularly, this invention concerns an improved safety needle for use with hypodermic syringes to allow the needle to be exposed for use and thereafter covered for disposal in a safety appliance, all without bringing one's hands into close proximity with the needle.

2. Description of the Prior Art

Everyone knows about hypodermic syringes and the sharp needles used in conjunction therewith. These hollow needles are inserted under the skin, usually intramuscularly or intravenously, to inject liquids and medications into our bodies and to withdraw blood from our veins. In all these cases, the advantages of the needle outweigh the disadvantages of the momentary pain encountered with their use.

That was all before AIDS, E-bola virus and other deadly pathogens/spread into populated centers of the world. With the advent of these diseases, the hypodermic needle and its uses have taken on an ominous tone. These pathogens spread through fluids and the hypodermic needle has become a major factor in transmitting the disease, either through sharing needles among drug users or in administering medications to the body. Accidental needle sticks during the application of medication or during the removal of body fluids has placed the health care worker at an increased risk. In particular, emergency treatment situations, such as at accident scenes or in emergency rooms have much higher incidence of needle sticks due to the need for rapid treatment and the lack of a controlled situation.

The prior art has attacked the spread of AIDS, as well as other body-fluid borne diseases such as hepatitis and venereal disease, with the use of a rigid sheath into which the new needle is housed during delivery and removed during use, as well as into which the used needle is inserted before it is discarded in a safe waste container. Unfortunately, this practice has not proven to be entirely safe, mainly because those using the needles often miss the entrance hole into the sheath, either through mere poor eyesight or because of being bumped or jostled during manipulation and stick themselves in the finger. More than one person has infected themselves in this manner.

In some care facilities, rules have been promulgated to prevent those handling the needles from having to insert them into a safety sheath before discarding. After the needles is used, it is merely inserted through a large opening in the top of a safety storage vessel. Even this has proven to be ineffective, in some cases, when personnel drop the needles after use and they stick in the user or someone near by. Accordingly, there is a need to prevent "stickers" by changing the mechanism by which the needles are handled.

SUMMARY OF THE INVENTION

This invention is an entirely new idea in the handling of hypodermic syringes. The invention concerns a device into which the needle is inserted and locked in fluid-tight position therein. In this device, the sharp tip of the needle is carried in a first bore and covered over by a cap. The cap contains a second bore which is, in normal repose, out of rotational alignment with the first bore thereby insuring that the sharp needle tip is completely covered over. In a region near the base of the needle, a mechanism is positioned for rotational movement so as to bring the first and second bores into alignment and subsequently is retracted rearward of the needle to cause a covering over the needle to be retracted rearward from the sharp tip and thereby exposing a length of the needle. The needle is now ready for use.

Following use of the needle, i.e., withdrawal from therein or muscle of the patient, either the same mechanism is automatically unlatched and urged forward to cover the entire length of the needle and cause the second bore in the cap to rotate out of alignment with the first bore carrying the sharp tip so as to once again completely cover the sharp tip, or a slight flick of the thumb against the collar will disengage a latch and a spring action in the mechanism will undertake the same action. In utilizing this invention, one need not bring their hands, fingers or any portion thereof into proximity of the needle for the mechanism operates to uncover and then automatically re-cover the needle and its tip.

Accordingly, the main object of this invention is an improved safety needle having the ability of uncovering and exposing the needle for use and then re-covering and capping the needle for discard, all without causing or requiring the operator's hands or fingers to enter the proximity of the needle or its sharp end. Other objects of the invention include a device made completely of plastic that may be rendered sterile through ordinary and low-cost sterilization operations; a device that may be used with a wide variety of sizes and lengths of needles; a device that is inexpensive to manufacture; a device that utilizes a small rotary force and short retracting movement to uncover and expose the operative length of a hypodermic needle; a device that automatically resets itself into a fully-safe position upon withdrawal of the needle from the patient's body; a device that is simple to use and does not require extensive training before placing into the daily routine of medical personnel.

These and other objects of the invention will become more apparent upon reading the following description of the preferred embodiments taken together with the drawings appended hereto. The scope of protection sought by the inventors may be gleaned from a fair reading of the claims that conclude this specification.

DESCRIPTION OF THE DRAWINGS

FIGS. 2 is an illustrative view showing the device of this invention retains the needle in a first position out of symmetry with the aperture through which it passes when activated;

FIG. 3 is the same illustration as FIG. 2 with the needle being placed in symmetry with the aperture for passage therethrough;

FIG. 4a is a graph of the axial force placed upon the cap of this invention as a function of the position of the inner members during flexing;

FIGS. 4b through 4d are illustrative views of the inner members of the invention shown in different flexing positions;

DESCRIPTION OF THE PREFERRED EMBODIMENT

Figure 1:
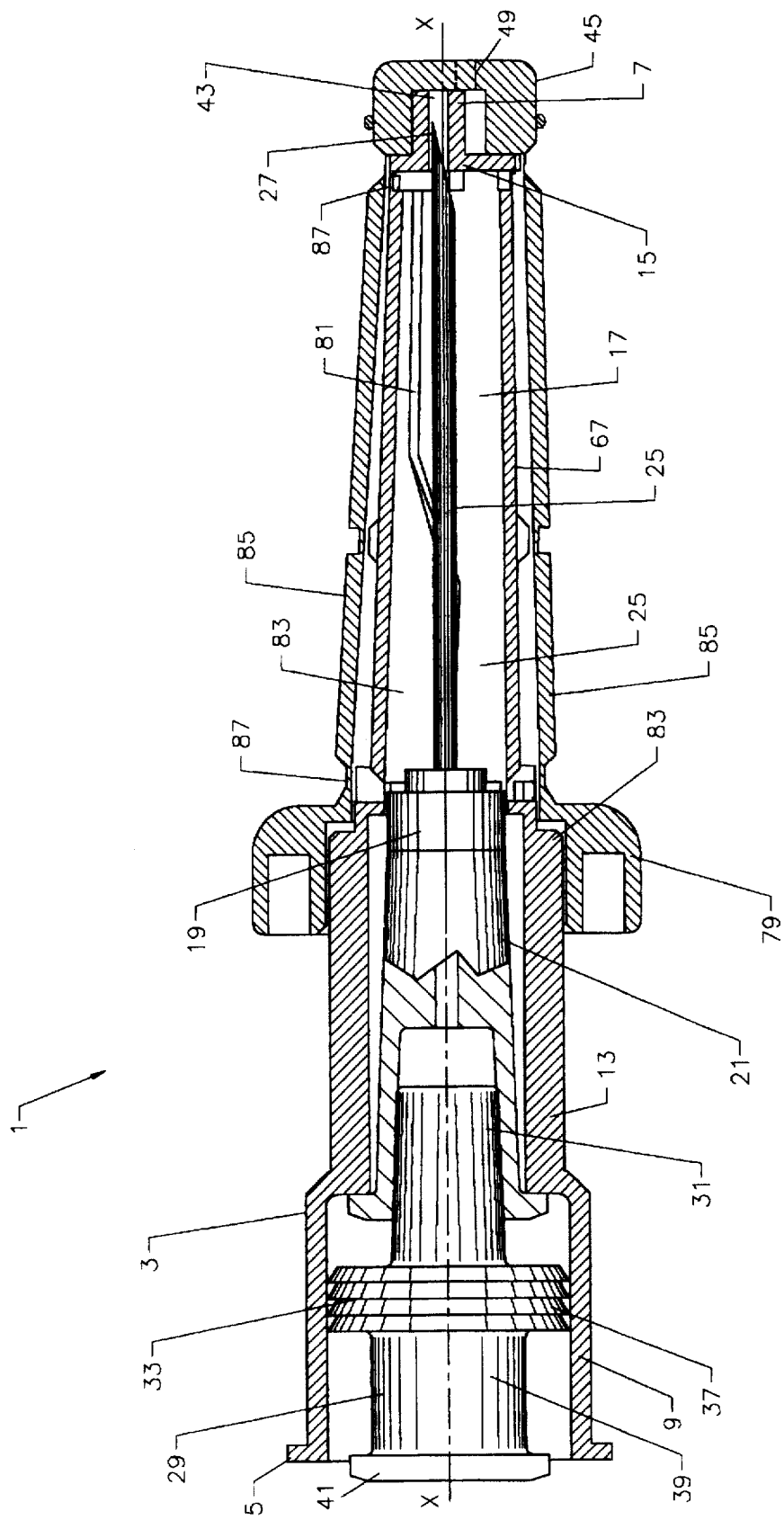
FIG. 1 is a side, partially sectional view of the various components which make up the safety needle of this invention.
Figure 10:
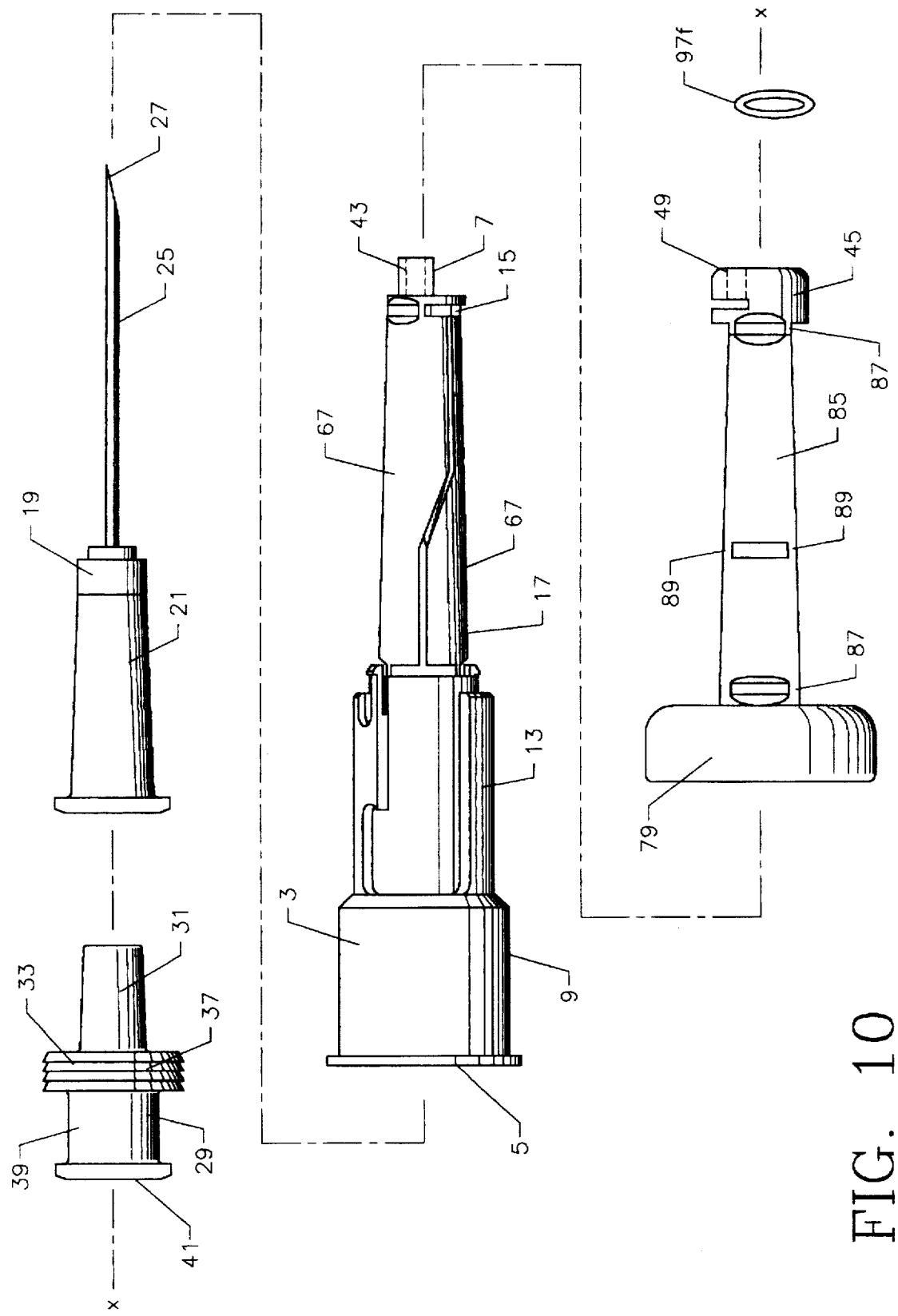
FIG. 10 is an exploded view of the parts of the preferred embodiment of this invention.

Turning now to the figures wherein like elements are identified with like numerals throughout the 27 figures, FIGS. 1 and 10 show the preferred embodiment of the improved safety needle invention 1 of this invention to comprise an elongated needle base 3 terminated by a proximal end 5 and a distal end 7 in spaced apart relation. Base 3 is further comprised of a hollow plug sleeve 9 extending from said proximal end 5 to an interim sleeve 13 of somewhat narrower diameter, and then to a nose 15, located at said distal end 7 through at least one elongated inner member 17 about which more will be discussed later in this specification.

A hypodermic needle assembly 19, comprising a tapered hollow hub 21 and a very slender metal tube or needle 25 extending from the narrower end of hub 21 to a sharp needle tip 27, is insertable in needle base 3, as shown in FIG. 1 and held therein by a needle plug 29. Plug 29 comprises a tapered front end section 31, for insertion in needle hub 21 to form a fluid-tight seal therebetween, a spacing center section 33, containing skirted rings 37 to hold needle assembly 19 firmly within needle base 3, and a rear interconnect section 39 of a size and shape for interconnecting with the barrel of a standard syringe (not shown) through a syringe interface 41.

Nose 15 has formed therethrough, in an axial direction, a first bore 43 concentric with needle 25 and of a diameter allowing sliding passage therethrough of said needle. Nose 15 is supported, as will hereinafter be more clearly described, at a position to cover and carry sharp needle tip 27 therein when needle 25 is fully inserted in needle base 3.

As shown in FIG. 2, a cap 45 is rotatably positioned over nose 15 to cover first bore 43 (cap 45 is moved forward for better visualization) and has formed therethrough a second bore 49, of similar inside diameter as first bore 43, that remains out of alignment with first bore 43 when this invention 1 is in normal repose or a "safe" position. Cap 45 is rotatable between a first, safe position "a" (FIG. 2) wherein first and second bores 43 and 49 are out of alignment, thereby preventing passage of needle 25 and its sharp needle tip 27 through cap 45, and a second, armed position "b" (FIG. 3) placing said first and second bores 43 and 49 in full alignment to allow passage of needle 25 therethrough to expose sharp needle tip 27.

Figure 5:
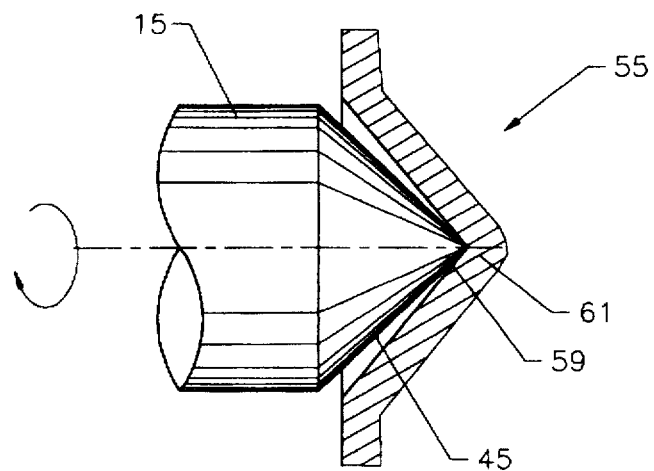
FIGS. 5, 6 and 7 are close-up, illustrative views of different embodiments of the needle centering means of this invention.
Figure 6:
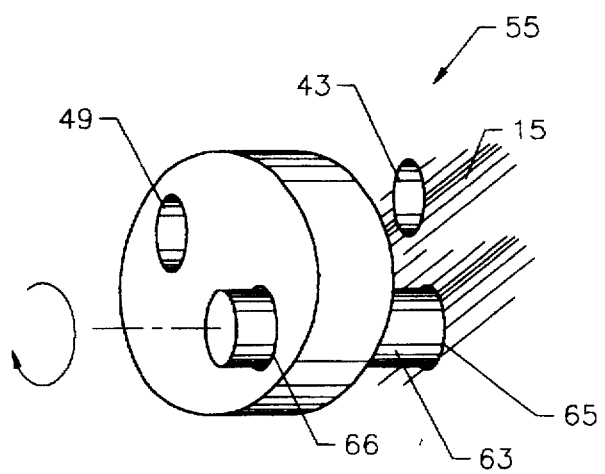
Figure 7:
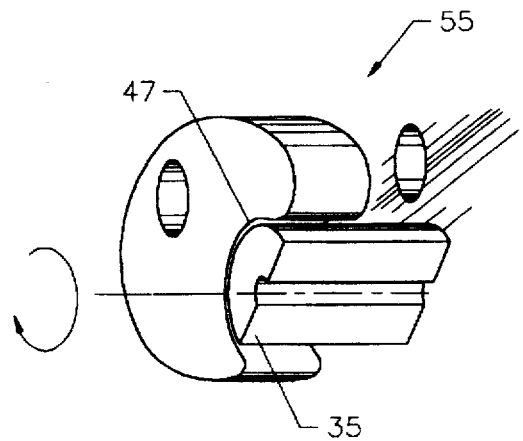
Figure 11:
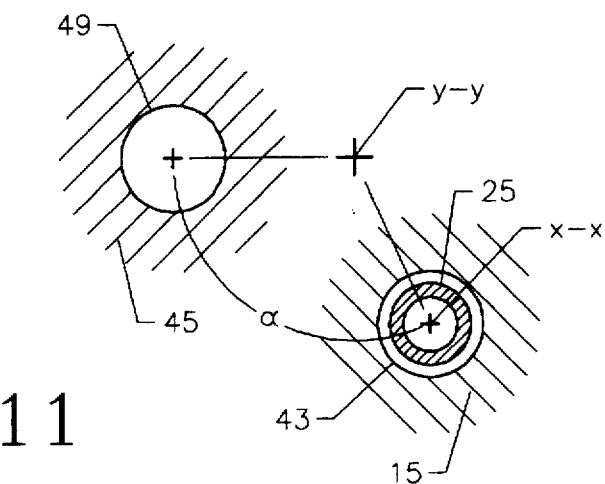
FIG. 11 is an illustrative view of the two axes of rotation of the nose and the cap of this invention; and, FIGS. 12a and 12b are illustrative views of the outer members of this invention and the various parts that make up these members.

Cap 45 is rotatable between two rotational stops "a" and "b", restricting the angle "α" (see FIG. 11) through which said rotary motion may occur, to bring second bore 49 into alignment with first bore 43. To align the respective bores in cap 45 and nose 15, a first centering means 55 is employed as shown in FIGS. 5 through 7. A wide variety of centering means 55 is usable herein. As shown in FIG. 5, means 55 includes the coincidence of a conical point 59 and a conical depression 61 formed respectively on the mating surfaces of nose 15 and cap 45. Another form of means 55 is shown in FIG. 6 to include an alignment pin 63, located on nose 15, pivotally interposed a first aperture 65 formed in nose 15 and a second aperture 66 formed in the mating surface of cap 45. Still another form of means 55 is shown in FIG. 7 to include the coincidence of a protruding arc segment 35 and a mating arc depression 47 formed respectively on the mating surfaces of nose 15 and cap 45. These parts may be revised or modified and still come within the scope and spirit of this invention.

As shown in FIGS. 4b, 4c, 4d, 12a and 12b, at least one, but preferably two, inner members 67 are interposed interim sleeve 13 and nose 15 and are connected respectively to nose 15 at a first hinge 69, and to sleeve 13 at a second hinge 73. As shown in FIG. 1, a collar 71 is slidingly mounted over interim sleeve 13. Inner members 67 are tubular in cross-section and capable of carrying a transitional load greater than that needed to align first and second bores 43 and 49, respectively. Preferably, inner members 67 are arranged in juxtaposed position on opposite sides of needle 25. Even further, said inner members 69 are shaped as substantially partial tubular segments arranged in juxtaposed relationship to form, as shown in FIGS. 4b, 4c, and 4d, a tubular structure about needle 25.

The reason two tubular members are preferred is because the tubular sections tend to want to stay tubular. When inner members 67 are buckled, they fold in a line "e—e", that is transverse to their longitudinal axis, as shown in FIGS. 4b and 4c. In the area of the buckling they will deform in two ways: first, the tubular section is straightened; secondly, it is folded almost in half along line "e—e". The energy inputted to inner members 67, stored in the "fold-in-half" configuration, provides the driving force for the initial covering motion imparted to nose 15 and is shown in graphic form in FIG. 4a. The energy stored in the flattening portions of the tubular cross-sections is released only after the arms are practically straight, just when the arms are running out of energy. This extra power, occurring right at the end of the stroke, is one of the features that makes this invention unique. In order for it to work, a tubular section is required; about half of a tube seems to work best. If the tubular section is a smaller fraction, then there is less energy to store, as the power to deform it to a flat shape is markedly less.

Inner members 67 may be formed in numbers other than one or two, however, two appear to produce the effects desired in this invention. One method of forming said inner, tubular member segments is from a tubular element by selectively slitting portions thereof; another is by molding them to shape; and another method is to selectively slit and cut away various portions from a tubular element. Further, to obtain the desired effects of this invention, it is preferred that tubular inner members 67 define, as shown in FIG. 10, a spiral along the central axis x—x of needle base 3 from distal end 7 to needle base 3, and in the same rotational direction as is required to rotate cap 45 from first position "a" to its second, armed position "b".

Figure 12A:
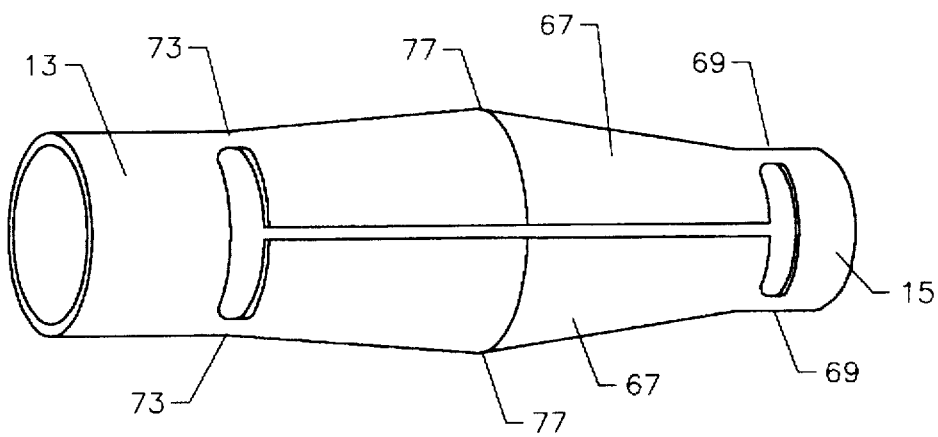
Figure 12B:
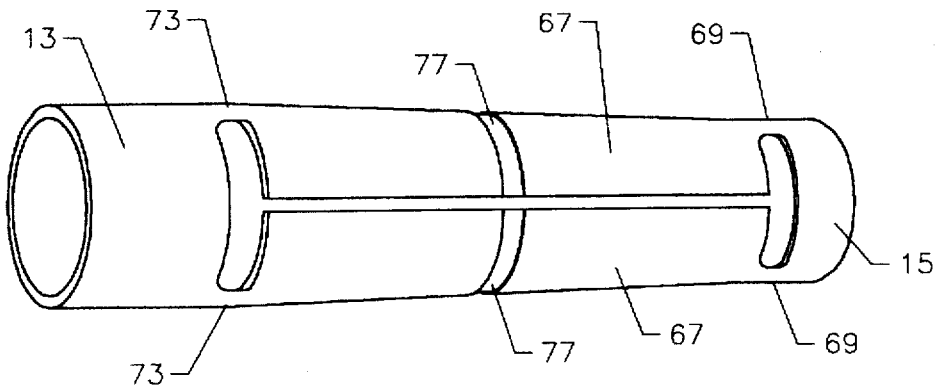

It is important that inner members 67 buckle outward so as not to interfere with movement of needle 25. This may be accomplished by forming an area 77 (see FIG. 12a) that are spaced-apart from a straight line midway between hinges 69 and 73, or by making area 77 an area of reduced cross-section on said inner members 69, as shown in FIG. 12b, preferably midway between hinges 69 and 73 through which members 69 are attached respectively to nose 15 and needle base 3.

As shown in FIG. 10, a collar 79 is slidingly positioned over the forward end of interim sleeve 13 and retained against rearward movement by a neck 81 that is slidingly mounted against a shoulder 83 formed at the front of sleeve 13.

At least one, but preferably a pair, of outer members 85 is interposed and connected through hinges 87 respectively to cap 45 and collar 79 and are of a size and shape capable of carrying a torsional load greater than that needed to rotate cap 45 to align first and second bores 43 and 49. When employing two outer members 85, it is preferred to arrange them juxtaposed and positioned on opposite sides of needle 25 outboard of inner members 67.

In the preferred embodiment and as shown in FIG. 1, outer members 85 comprise substantially flat beams and are buckleable at interim hinges 89, when needle 25 is inserted into the flesh of a person. Outer members are connected to cap 45 and collar 77 by hinges 87.

While one inner member 67 and one outer member 85 may perform the basic movement desired in improved safety needle invention 1, it is preferred that a pair of inner members 67 are employed along with a pair of outer members 85 and said members spaced-rotationally apart from each other sufficient to permit both said members to buckle outward in a direction along needle 25 without touching each other. Buckling of inner members 79 and outer members 87 may be controlled by use of forming areas of reduced cross-section or intermediate hinges 77 for inner members 67, as aforesaid, and a similar area 91 for outer members 85 as shown in FIG. 1.

Figure 8A:
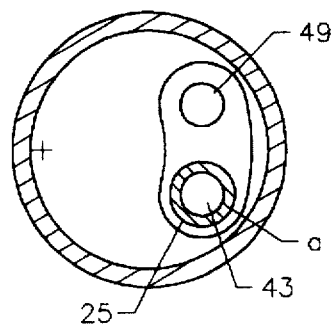
FIGS. 8a through 8k are illustrative end views of different examples of the means of rotating two parts with respect to each other under tension.
Figure 8B:
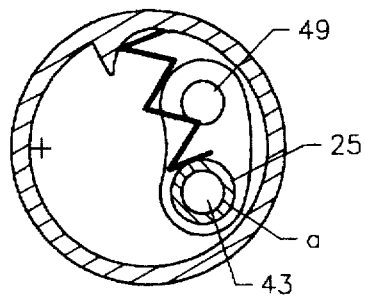
Figure 8E:
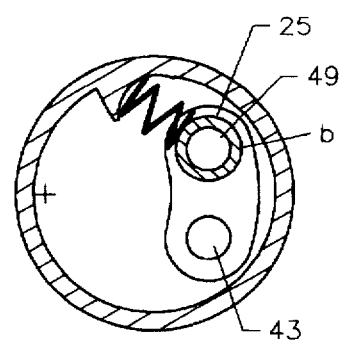
Figure 8C:
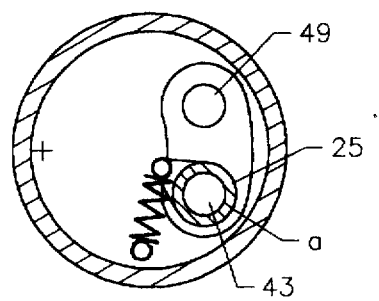
Figure 8F:
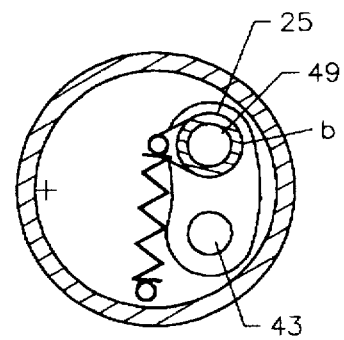
Figure 8D:
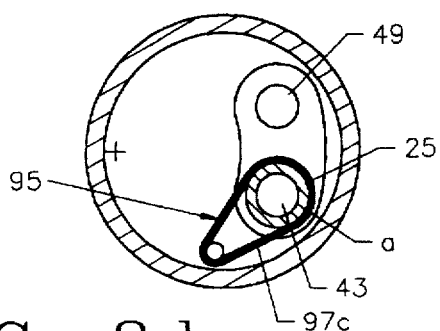
Figure 8G:
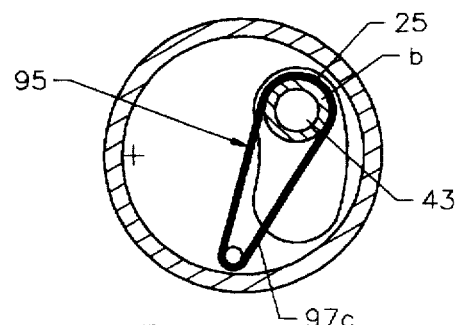
Figure 8H:
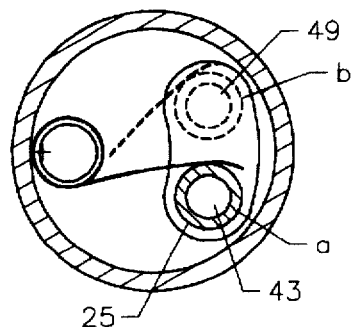
Figure 8I:
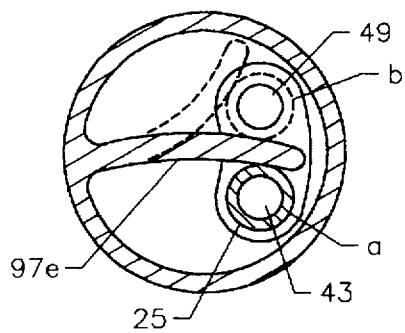
Figure 8J:
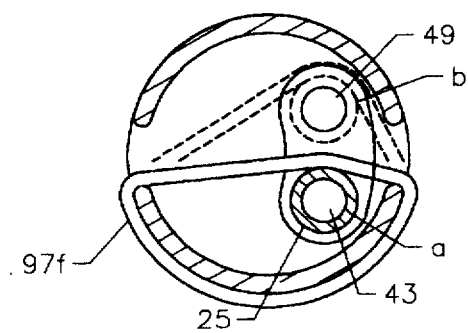
Figure 8K:
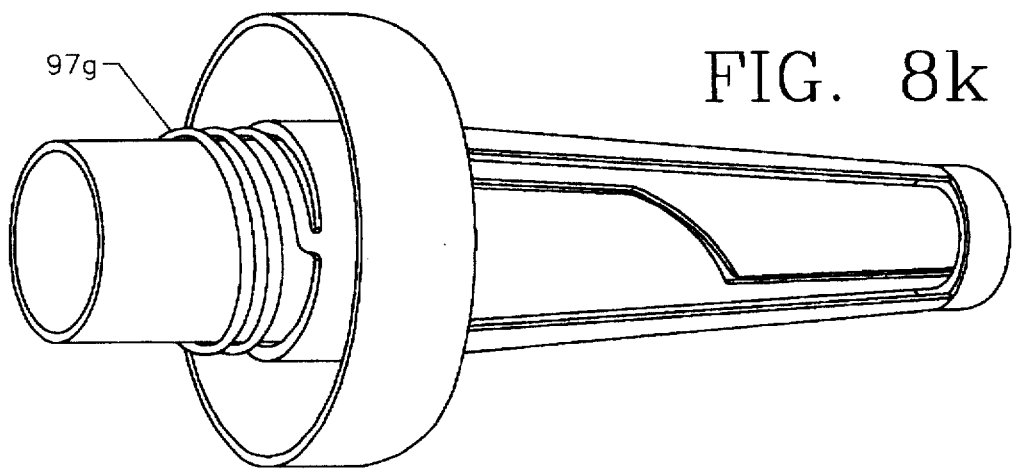

A bias means 95 is required to retain cap 45 in said first position "a" that can be overcome by manual delivery of a torsional force or twisting to collar 79 to move into second position "b" and bring second bore 49 into alignment with first bore 43.. As shown in FIGS. 8a through 8k, bias means 95 may include a compression spring 97a (FIGS. 8b and 8d), a tension spring 97b (FIGS. 8c and 8f), and elastomeric material 97c (FIGS. 8d and 8g). FIGS. 8h shows a torsion spring 97d; FIG. 8i shows a leaf spring 97e; FIG. 8j shows an elastomeric band 97f; and, FIG. 8k shows a molded-in torsion spring 97g all acting between first bore 43 and cap 45. All of these embodiments use an axis of rotation y—y set apart from the major axis of rotation x—x of collar 77 (see FIG. 11). All of these bias means act along the axis x—x of needle base 3, to provide rotational force to retain first bore 43 and second bore 49 rotationally apart. Bias means 95 (and its other embodiments) may be made from the same material as cap 45 and, as shown in FIG. 8k, may be molded in the form of an integral spring 97h.

Spring 97f may be fashioned as an elastic "O" ring as shown in FIG. 8j. As shown, elastic "O" ring 97f is arranged on a plane perpendicular to axis x—x to increase in size when rotating cap 45 from first position "a" to second position "b". See FIG. 10.

Figure 9A:
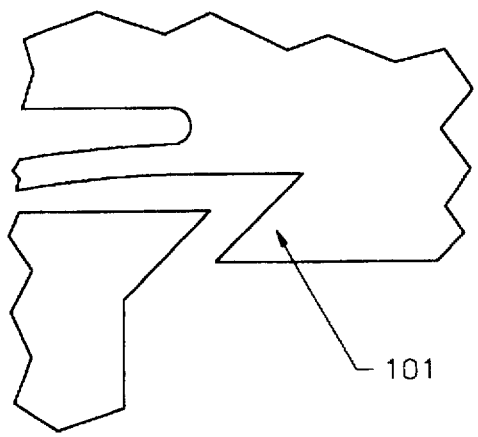
FIGS. 9a and 9b are illustrative views of rotary force means for urging the latch apart.
Figure 9B:
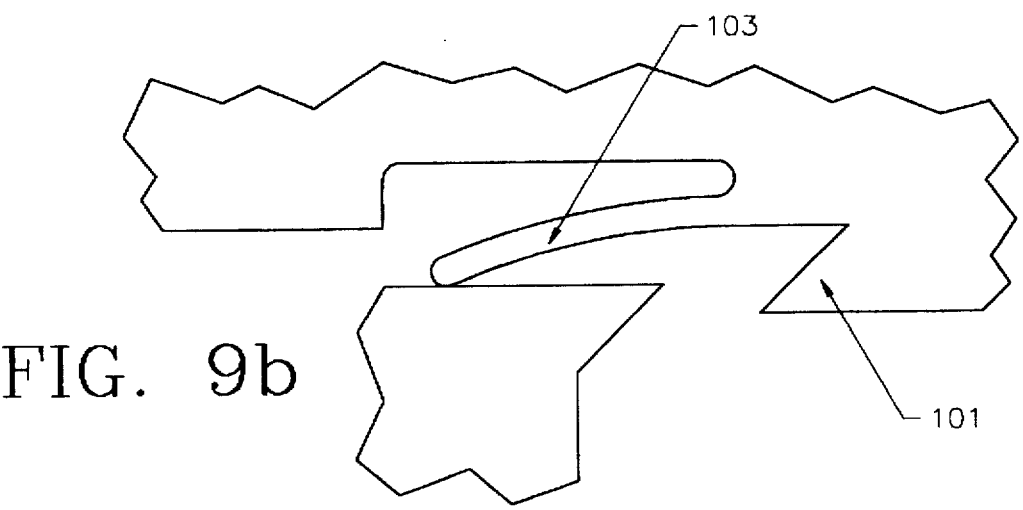

A latch 101 is provided, as shown in FIGS. 9a and 9b, to hold said bores 43 and 49 in said second, aligned, and armed position following overcoming of said bias means. Latch 101 is engaged when collar 79 is twisted on interim sleeve 13, to rotate cap 45 from first position "a" to second position "b" and align bores 43 and 49, and then retracted along sleeve to cause cap 45 to retract along needle 25 and uncover said needle and its tip 27. During this retraction, inner members 67 and outer members 85 deform outward, as shown in FIG. 4c, to allow uncovering of said needle.

In the preferred embodiment, as shown in FIG. 9a, latch 101 is located on needle base 3 and is subject to an axial force along needle 25 toward the sharp needle tip 27 thereof, and a rotary force is applied about the rotational axis x—x of said needle base 3, urging said latch apart. Said latch 101 is therefore released when a rotary force is applied to disengage said latch and cap 45 is urged by said axial force, toward and beyond sharp needle tip 25 and rotationally into first position "a". Latch 101 is released when the axial force is overcome and collar 79 is moved rearward. Collar 79 is thus only subject to the rotary force which disengages latch 101. The axial force can be overcome in two ways: cap 45 can contact the patient's skin or is released when one merely bumps collar 79 with the thumb.

This axial force is supplied by resilient bias means 95 acting between said needle base 3 and said first bore 43 urging said first bore away from needle base 3. The aforesaid axial force is preferably supplied by inner members 67. The rotary force is provided by either torsionally stiff outer members 85 or by a torsion spring 103, acting between needle base hub 21 and collar 79. Where torsion spring 103 is used, it is molded or inserted between hub 21 and collar 79 as shown in FIG. 8k.

This invention may be used along with an improved method of delivering medication through hypodermic injection utilizing a plunger body attached to needle base 3 and needle 25. The steps of this unique method include providing a collar 79 on needle base 3, interconnected cap 45 covering sharp needle end 27 of needle 25; rotating collar 79 on needle base 3 to cause inner members 67 and outer members 85 to rotate and align second bore 49 with first bore 43. Thereafter, pulling collar 79 back on needle base 3, buckling inner members 67 to a latching point where a length of the needle is exposed and latch 101 holds inner members 67 in buckled and folded configuration.

After either delivering the liquid medication through needle 25 or withdrawing bodily fluids therethrough, collar 79 automatically rotates in the reverse direction to decouple latch 101 and allow inner and outer members 67 and 85 to relax and unbuckle so as to move nose 15 forward over needle 25 and rotating cap 45 from second position "b" to first position "a" and covering needle sharp tip 27. If this is not accomplished automatically, a slight bump to collar 79 will disengage latch 101 and said members will complete the operation under their own power as hereinbefore described. The operator's hands never, at any time, descend below collar 79 and therefore do not encounter sharp needle tip 27.

Both inner members 67 and outer members 85 are preferably made of plastic using a wide variety of manufacturing processes such as injection molding. Inner members 67 are preferably made of plastic of sufficient size and cross-section to be capable of supporting a torsional load sufficient to rotate cap 45 with respect to collar 79.

In its preferred embodiment, inner members 67 and outer members 85 are placed at 90° to each other about needle 25. By considering a hypothetical envelope to be wrapped about outer component, one can see that by rotating collar 79 to align first and second bores 43 and 49, and then retracting collar 79 along needle base 3 away from sharp needle tip 27, inner members 67 and outer members 85 undergo buckling, whereby inner members 67 buckle without interference from outer members 85 and exceed the envelope traced by outer members 85.

While the invention has been described with reference to a particular embodiment thereof, those skilled in the art will be able to make various modifications to the described embodiment of the invention without departing from the true spirit and scope thereof. It is intended that all combinations of elements and steps which perform substantially the same function in substantially the way to achieve substantially the same result are within the scope of this invention.

What is claimed is:

1. An improved safety needle, comprising:
   a) a needle base, for fixing therein a rigid needle containing a hollow hub at one end, a hollow needle connected thereto and a sharp needle tip at the other end, said base defined by a proximal end and a distal end spaced-apart therefrom;
   b) said distal end of said needle base having formed therethrough a first bore concentric to said needle and carrying said sharp needle tip; and,
   c) a cap covering said first bore and rotatably positioned thereover, having formed therethrough a second bore;
   d) wherein said cap is rotatable between a first, safe position placing said first and second bores out of alignment and preventing passage of the needle and the sharp needle tip therethrough, and a second, armed position placing said first and second bores in alignment to allow passage of said needle therethrough to expose said sharp needle tip.

2. The improved safety needle of claim 1 wherein said first and second positions of said cap are defined by rotational stops which restrict the angle through which said rotary motion may occur.

3. The improved safety needle of claim 1 wherein said first and second bores are offset respectively from said needle base and said axis of rotation of said cap.

4. The improved safety needle of claim 1 further including means for aligning the central axis of said needle base distal end with the axis of rotation of said cap.

5. The improved safety needle of claim 4 wherein said means includes the coincidence of a conical point and a conical depression formed respectively on said needle base distal end and the adjacent surface of said cap.

6. The improved safety needle of claim 4 wherein said means includes a pin interposed said needle base distal end and said cap.

7. The improved safety needle of claim 4 wherein said means includes the coincidence of a protruding arc segment and a mating arc depression formed on said needle base distal end and the adjacent surface of said cap.

8. The improved safety needle of claim 1 wherein said rotation, between said cap and said needle base distal end, to bring said first and second bores into alignment, is transmitted from a region spaced-apart from said cap.

9. The improved safety needle of claim 8 further including a collar slidingly mounted on said needle base, intermediate said distal end and said proximal end thereof, for rotating about said base to effect rotation of said cap.

10. The improved safety needle of claim 1 further including at least one inner member interposed said needle base and said first bore and extending therebetween, said member being capable of carrying a torsional load greater than that needed to align said first and second bores.

11. The improved safety needle of claim 10 including two inner members in close, spaced-apart relation and positioned on opposite sides of the needle.

12. The improved safety needle of claim 10 wherein said inner member is of a length and tensile stiffness to restrain said first bore from extending beyond the sharp tip of the needle.

13. The improved safety needle of claim 11 wherein said inner members are substantially tubular segments, in close, spaced-apart facing relationship to form a tubular structure about the needle.

14. The improved safety needle of claim 13 wherein said tubular segments are formed about a tubular element by selectively slitting portions thereof.

15. The improved safety needle of claim 13 wherein said tubular segments are formed from a tubular element by selectively slitting and cutting away various portions thereof.

16. The improved safety needle of claim 13 wherein said tubular structure is substantially cylindrical in cross-section.

17. The improved safety needle of claim 13 wherein said tubular segments define a spiral along the central axis of said safety needle, from said distal end to said needle base, in the same rotational direction as is required to rotate said cap from said first position to said second position.

18. The improved safety needle of claim 13 wherein at least one of said tubular segments urges said first bore into covering position over the sharp needle tip.

19. The improved safety needle of claim 13 further including elongated edges, defining said tubular segments, said edges defining a spiral along the central axis of said safety needle, from said distal end to said needle base, in the same rotational direction as is required to rotate said cap from said first position to said second position.

20. The improved safety needle of claim 11 wherein said inner members are substantially flat beams arranged about the needle.

21. The improved safety needle of claim 10 wherein said inner member is buckleable, under hand-pressure, in a direction along the central axis of the needle.

22. The improved safety needle of claim 10 further including a buckleable portion formed on said inner member spaced-apart from a straight line interconnecting the respective terminal ends of said member.

23. The improved safety needle of claim 10 further including an area of reduced cross-section formed on said inner member to promote buckling of said member.

24. The improved safety needle of claim 9 including at least one outer member interposed said collar and said cap and extending therebetween, said member being capable of carrying a torsional load greater than that needed to align said first and second bores.

25. The improved safety needle of claim 9 including two outer members in close, spaced-apart relation and positioned on opposite sides of the needle.

26. The improved safety needle of claim 25 wherein said two outer members comprise substantially flat beams.

27. The improved safety needle of claim 24 wherein said outer member is buckleable, under hand-pressure, in a direction along the central axis of the needle.

28. The improved safety needle of claim 9 further includes:
   a) at least one buckleable inner member interposed said needle base and said first bore and extending therebetween; and,
   b) at least one buckleable outer member interposed said collar and said cap;
   c) wherein said members are spaced-apart from each other sufficient to permit both said members to buckle in a direction along the needle without touching each other.

29. The improved safety needle of claim 28 further including a buckleable portion formed on both said inner member and said outer member spaced-apart from straight lines interconnecting the respective terminal ends of said members.

30. The improved safety needle of claim 29 wherein said buckleable portions include an area of reduced cross-section in said members to promote buckling of said members under hand-pressure.

31. The improved safety needle of claim 9 further including bias means to retain said cap in said first, safe position that can be overcome by manual delivery of a torsional force to bring said cap into said second, armed position.

32. The improved safety needle of claim 31 wherein said bias means includes a spring, acting between said first bore and said cap and along the axis of said needle base, to provide rotational force to retain said first bore and said second bore rotationally apart.

33. The improved safety needle of claim 32 wherein said spring is made of the same material as said cap and is permanently attached to said needle base.

34. The improved safety needle of claim 32 wherein said spring is made of the same material as said cap and is permanently attached to said collar.

35. The improved safety needle of claim 31 wherein said bias means includes an elastic ring arranged on a plane perpendicular to the axis of rotation of said cap to be increased in size when rotating said cap from said first position to said second position.

36. The improved safety needle of claim 31 wherein said bias means is interposed said needle base and said collar to retain said cap in said first position.

37. The improved safety needle of claim 31 wherein said bias means is the needle.

38. The improved safety needle of claim 1 further including bias means to urge said first and second bores in said first position and a latch to hold said bores in said second, armed position when said bias means is overcome.

39. The improved safety needle of claim 38 wherein said latch is located on said needle base and is subject to an axial force along the needle toward the sharp needle tip thereof, and a rotary force about the rotational axis of said needle base, urging said latch apart, said latch thereby releasing when rotary force disengages said latch and said cap is urged by said axial force toward, and beyond, the sharp needle tip and rotationally into said first position.

40. The improved safety needle of claim 39 wherein said axial force is supplied by resilient bias means acting between said needle base and said first bore urging said first bore away from said needle base.

41. The improved safety needle of claim 39 wherein said rotary force is supplied by resilient bias means acting between said needle base and said first bore urging said latch in rotary motion about the rotational axis of said needle base.

42. The improved safety needle of claim 39 wherein said axial force and said rotary force are supplied by the same resilient bias means.

43. The improved safety needle of claim 39 wherein said resilient bias means includes two inner members in close, spaced-apart relation, positioned on opposite sides of the needle, interposed said needle base and said first bore, and extending therebetween providing an axial force urging said first bore from said needle base.

44. The improved safety needle of claim 39 wherein said rotary force is provided by a torsion spring, acting between said needle base and a rotatable collar, said collar connected to said cap with torsionally stiff outer members.

45. The improved safety needle of claim 39 wherein said rotary force is provided by a leaf spring, mounted on said needle base and acting between said base and said cap through torsionally stiff outer members.

46. The improved safety needle of claim 39 wherein said rotary force is provided by inner members connecting said needle base to said first bore.

47. The improved safety needle of claim 1 further including a plug for partial insertion in said hub in fluid-tight relationship and securely gripping said hub to said needle base, said plug having a bore formed therein for passage of fluid from a hypodermic syringe barrel, attached thereto, to the needle.

48. An improved method of delivering medication through hypodermic injection with a safety needle, utilizing a plunger body attached to a needle base and needle, the distal end of which is sharpened for insertion into a patient, said needle protected from accidental needle sticks with a safety device, comprising the steps of:
   a) providing a collar on said needle base interconnected a cap covering said sharp end of said needle;
   b) rotating said collar on said base to retract said cap and expose said sharp end of said needle;
   c) pulling said collar rearward on said needle base to a latching point where a length of the needle is exposed;
   d) delivering said medication through said needle; and,
   e) rotating said collar to unlatch said safety device and allow said needle to be re-covered by said cap.

49. The improved method of delivering medication of claim 48 further including the step of drawing said medication from a supply container into said plunger body before delivering said medication.

50. An improved guard for a hypodermic needle, comprising:
   a) a first, inner component including a needle base for fluid-tight receipt therein of the hollow hub of a needle, the needle having a sharp needle tip spaced-apart from the hub, and a first bore carrying the sharp needle tip therein; and,
   b) a second, outer component of larger size than said inner component and substantially concentrically in communication thereover, said second component including a second bore capable of being brought into alignment with said first bore to allow exposure of the needle through a rotary motion of said second component about said first component.

51. The improved guard of claim 50 wherein both said components are made of plastic.

52. The improved guard of claim 50 wherein both said components are made of plastic and contain hinged sections molded therein.

53. The improved guard of claim 50 wherein said inner and outer components include resilient means urging said first and said second bores into misalignment.

54. The improved guard of claim 53 wherein said resilient means is a torsion spring acting between said inner and outer components.

55. The improved guard of claim 53 wherein said resilient means is made of the same material as said inner compartment and molded integral therewith.

56. The improved guard of claim 53 wherein said resilient means is made of the same material as said outer component and molded integral therewith.

57. The improved guard of claim 53 wherein said resilient means is a linear spring acting between said inner and outer components at a distance from the common rotary axis therebetween.

58. The improved guard of claim 53 wherein said resilient means is a compression spring acting between said inner and outer components at a distance from the common rotary axis therebetween.

59. The improved guard of claim 53 wherein said resilient means is a tension spring acting between said inner and outer components at a distance from the common rotary axis therebetween.

60. The improved guard of claim 53 wherein said resilient means is elastic material acting between said inner and outer components at a distance from the common rotary axis therebetween.

61. The improved guard of claim 53 wherein said resilient means is an elastomeric ring acting between said inner component and said outer component at a distance from the common rotary axis therebetween.

62. The improved guard of claim 61 wherein said resilient means is a spring element acting through an arc and delivering force at a distance from the common rotary axis of said inner and outer components, other than in a purely radial direction from said common rotary axis.

63. The improved guard of claim 61 wherein said resilient means is a leaf spring made of the same material as said inner component and molded integral therewith.

64. The improved guard of claim 61 wherein said resilient means is a leaf spring made of the same material as said outer component and molded integral therewith.

65. The improved guard of claim 50 wherein said inner component further includes at least two inner members, interposed said needle base and said first bore and extending therebetween said members capable of supporting a torsional load sufficient to rotate said inner component with respect to said outer component through said rotary motion.

66. The improved guard of claim 65 wherein said inner members are predisposed to buckle when subjected to a pre-determined load in the line of action along the needle.

67. The improved guard of claim 65 wherein said inner members are predisposed to buckle in an area of reduced cross-sections formed therein.

68. The improved guard of claim 65 wherein said inner members are predisposed to buckle due to the combination of:
   a) a segment of said inner members defining a spiral about and along the longitudinal axis of said first component, winding from said needle base towards said first bore, against the direction of rotation used to align the sharp needle tip in said first bore; and,
   b) a rotation of said outer component with respect to said inner component greater than that required to align said first bore with said second bore, said rotation causing said inner members to deform in a manner which increases their respective distances from the sharp tip of the needle.

69. The improved guard of claim 50 wherein said first, inner component includes a tubular passage connecting said needle base and said first bore by at least two inner members, said members being predisposed to their undeformed shape and urge said first bore toward the sharp needle tip when said inner members are buckled along said needle.

70. The improved guard of claim 50 wherein said second, outer component includes:
   a) a cap covering said first bore and rotatably positioned thereover, having formed therethrough a second bore;
   b) a rotatable collar located near the proximal end of said needle base; and,
   c) at least two outer members connecting said collar to said cap in a manner which will support the torsional load required to rotate said second bore into alignment with said first bore.

71. The improved guard of claim 70 wherein said outer members are predisposed to buckle when subjected to a predetermined compressive load in a line of action along said needle.

72. The improved guard of claim 70 wherein said outer members are predisposed to buckle in an area of reduced cross-section formed therein.

73. The improved guard of claim 70 wherein said outer members are predisposed to buckle due to a portion of said outer members being disposed further from the needle than a straight line defined by the connection points of said outer members with said rotatable collar and said bore.

74. The improved guard of claim 70 wherein said outer members do not completely surround said inner members, permitting said inner members to exceed the envelope traced by said outer members when said inner members are buckled.

75. The improved guard of claim 50 wherein said inner component is formed separate from the needle.

76. The improved guard of claim 50 wherein said inner component is further defined by a proximal end and a distal end, mutually spaced-apart therefrom and said proximal end is adapted to receive the rigid needle therein.

77. The improved guard of claim 50 wherein the rigid needle, comprising a hollow hub, hollow needle attached thereto, and a sharp needle tip is secured within said inner component with a hollow plug, insertable in said needle base, and sealed therewith in fluid-tight relationship allowing liquid to pass leak-free through said plug to the needle tip.

78. The improved guard of claim 76 further including a hollow plug for insertion in said needle base, behind the needle, allowing fluid communication therethrough to the needle.

* * * * *